(12) United States Patent
Keane

(10) Patent No.: US 6,226,088 B1
(45) Date of Patent: *May 1, 2001

(54) OPTICAL WEB DEFECT DETECTION SYSTEM

(76) Inventor: Barry P. Keane, 1704 Keowee Lakeshore Dr., Seneca, SC (US) 29672

(*) Notice: Subject to any disclaimer, the term of this patent is extended or adjusted under 35 U.S.C. 154(b) by 0 days.

This patent is subject to a terminal disclaimer.

(21) Appl. No.: 09/240,533

(22) Filed: Jan. 29, 1999

(51) Int. Cl.[7] ................................................. G01N 21/898
(52) U.S. Cl. ....................................... 356/430; 356/238.2
(58) Field of Search ...................... 356/429, 430, 356/431, 238.1, 238.3, 238.2, 242; 250/559.46, 559.24, 559.26, 559.45, 559.48

(56) References Cited

U.S. PATENT DOCUMENTS

| | | |
|---|---|---|
| H1616 | 12/1996 | Wolfe . |
| 3,206,606 | 9/1965 | Burgo et al. . |
| 3,453,053 | 7/1969 | Gunn-Russell . |
| 3,612,702 | 10/1971 | Troll . |
| 3,618,063 * | 11/1971 | Johnson ................................ 356/431 |
| 3,693,021 * | 9/1972 | Lake, Jr. et al. ...................... 356/430 |
| 3,754,146 * | 8/1973 | Chow .................................. 250/559.48 |
| 3,859,538 | 1/1975 | Mannonen . |
| 3,931,525 * | 1/1976 | Clarke ................................. 356/430 |
| 3,958,127 | 5/1976 | Faulhaber et al. . |
| 3,972,624 * | 8/1976 | Klein et al. .......................... 356/237 |
| 3,975,644 * | 8/1976 | Scharf ................................. 356/430 |
| 4,011,457 | 3/1977 | Wolf . |
| 4,110,047 * | 8/1978 | Takahashi ............................ 356/430 |
| 4,131,803 | 12/1978 | Takematsu et al. . |
| 4,414,476 | 11/1983 | Maddox et al. . |
| 4,506,969 * | 3/1985 | Baker .................................. 356/385 |
| 4,656,360 | 4/1987 | Maddox et al. . |
| 4,728,800 | 3/1988 | Surka . |
| 4,788,756 | 12/1988 | Leitner, Sr. . |
| 4,944,505 * | 7/1990 | Sherman, III ....................... 356/383 |
| 4,982,105 * | 1/1991 | Takahashi ............................ 356/431 |
| 5,035,030 | 7/1991 | Pellari . |
| 5,043,588 * | 8/1991 | DiGrande et al. ................... 356/386 |
| 5,243,402 * | 9/1993 | Weber et al. ........................ 356/429 |
| 5,243,408 | 9/1993 | Whitman, III . |
| 5,287,742 | 2/1994 | Aihara et al. . |
| 5,497,235 | 3/1996 | Bell . |
| 5,555,611 | 9/1996 | Lyczek . |
| 5,621,220 | 4/1997 | Muehlenhein et al. . |
| 5,854,683 | 12/1998 | Keane . |
| 6,084,681 * | 7/2000 | Keane ................................. 356/430 |

OTHER PUBLICATIONS

Manual describing input/output boards, pp. 4, 5 and 32, published before Oct. 24, 1996.

* cited by examiner

Primary Examiner—Hoa Q. Pham
(74) Attorney, Agent, or Firm—Nelson Mullins Riley & Scarborough, LLP

(57) ABSTRACT

An optical web defect detection system includes a light source, a detector disposed with respect to the light source so that the detector receives light modulated by the web, and a control mechanism in operative communication with the detector. The control mechanism receives an output signal from the detector to detect a defect in the web based thereon. The detector may be disposed so that it receives light modulated by the web and emitted by the light source at an oblique angle with respect to a plane defined by the web. A first detector may be disposed at a first distance from the web less than a second distance at which a second detector is disposed from the web. A shift mechanism may reciprocally remove the detector in a path parallel to a plane defined by the web.

14 Claims, 15 Drawing Sheets

OPTICAL WEB DEFECT DETECTION SYSTEM

BACKGROUND OF THE INVENTION

The present invention relates to a system for detecting defects in a moving web. Webs, for example textile webs, may often include defects, for example yarn width variations, mispicks, double picks, machine stop marks, and pile irregularities, which are not readily detectable by a human operator. These defects sometimes become apparent only during downstream processing steps, for example dying, or after the fabric is shipped to a customer. According, it is desirable to detect such defects at a relatively early production stage.

Automatic web defect detection systems are known which employ photodetectors disposed with respect to a light source and the moving web to detect defects from the interference between the web and light from the light source. Calibration of such systems so that these photodetectors receive an optimal light signal may sometimes be difficult, particularly as the web or ambient conditions change.

SUMMARY OF THE INVENTION

The present invention recognizes and addresses disadvantages of prior art constructions and methods.

Accordingly, it is an object of the present invention to provide an improved optical web detection system.

This and other objects are achieved in one preferred embodiment of the present invention by an optical web defect detection system. The system comprises a light source and a detector disposed with respect to the light source so that the detector receives light modulated by a moving web and emitted by the light source at an oblique angle with respect to a plane defined by the web. The detector outputs a signal corresponding at least in part to the modulated light. A control mechanism is in operative communication with the detector. The control mechanism receives the signal to detect a defect in the web based on the signal.

In another preferred embodiment, an optical web defect detection system includes a light source and a first detector disposed with respect to the light source, and at a first distance from a moving web, so that it receives light modulated by the web. The first detector outputs a first signal corresponding at least in part to the first modulated light. A second detector is disposed with respect to the light source, and at a second distance from the web greater than the first distance, so that the second detector receives light modulated by the web. The second detector outputs a second signal corresponding at least in part to the modulated light. A control mechanism is in operative communication with the first detector and the second detector. The control mechanism receives the first signal and the second signal to detect defects in the web based thereon.

In another preferred embodiment, an optical web defect detection system includes a light source and a detector disposed with respect to the light source so that the detector receives light modulated by a moving web proximate the light source. The detector outputs a signal corresponding at least in part to the modulated light. A control mechanism is in operative communication with the detector and the adjustment mechanism. The control mechanism receives the signal to detect a defect in the web based thereon. A shift mechanism is in operative communication with the detector and is configured to reciprocally move the detector in a path parallel to a plane defined by the web and disposed at an oblique angle with respect to a line transverse to the moving direction of the web.

The accompanying drawings, which are incorporated in and constitute a part of this specification, illustrate one or more embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended drawings, in which.

Figure 1:
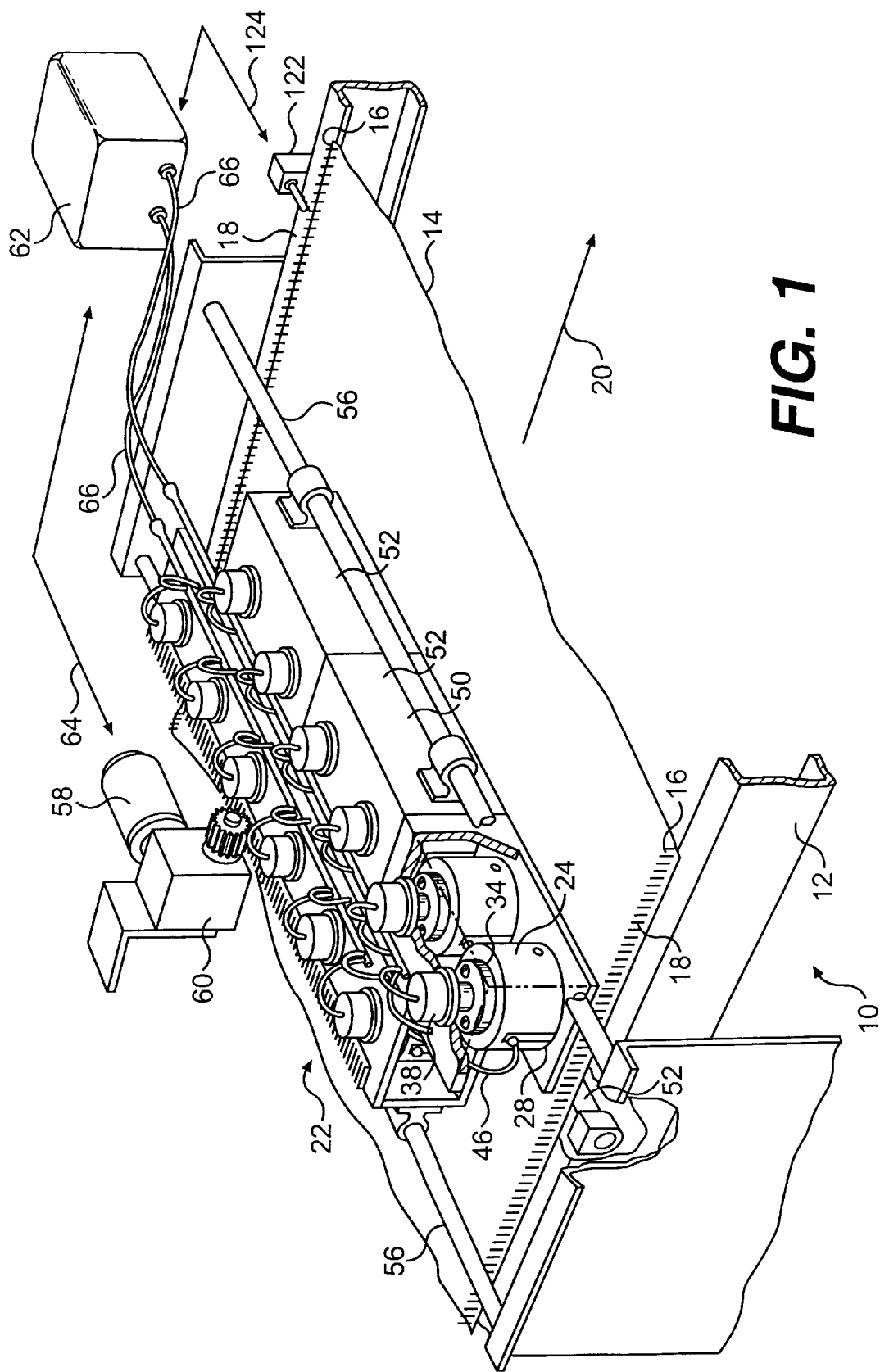
FIG. 1 is a partial perspective view of an embodiment of an optical web defect detection system constructed in accordance with the present invention.

Repeat use of reference characters in the present specification and drawings is intended to represent same or analogous features or elements of the invention.

DETAILED DESCRIPTION OF PREFERRED EMBODIMENTS

Reference will now be made in detail to presently preferred embodiments of the invention, one or more examples of which are illustrated in the accompanying drawings. Each example is provided by way of explanation of the invention, not limitation of the invention. In fact, it will be apparent to those skilled in the art that various modifications and variations can be made to the present invention without departing from the scope or spirit of the invention. For instance, features illustrated or described as part of one embodiment can be used on another embodiment to yield a still further embodiment.

The present invention is concerned with an optical web defect detection system. Accordingly, FIG. 1 depicts a web handling system 10 including a frame 12 securing a textile web 14 at selvages 16 by pins 18 to move web 14 in a longitudinal direction indicated at arrow 20. System 10 also includes an optical web defect detection system, indicated generally at 22, which includes a plurality of detectors 24 disposed proximate each other to extend substantially across the web. The detectors extend across the web over that part of the web for which detection of defects is desirable. Thus, for example, the detectors might not extend over the selvages.

Figure 4:
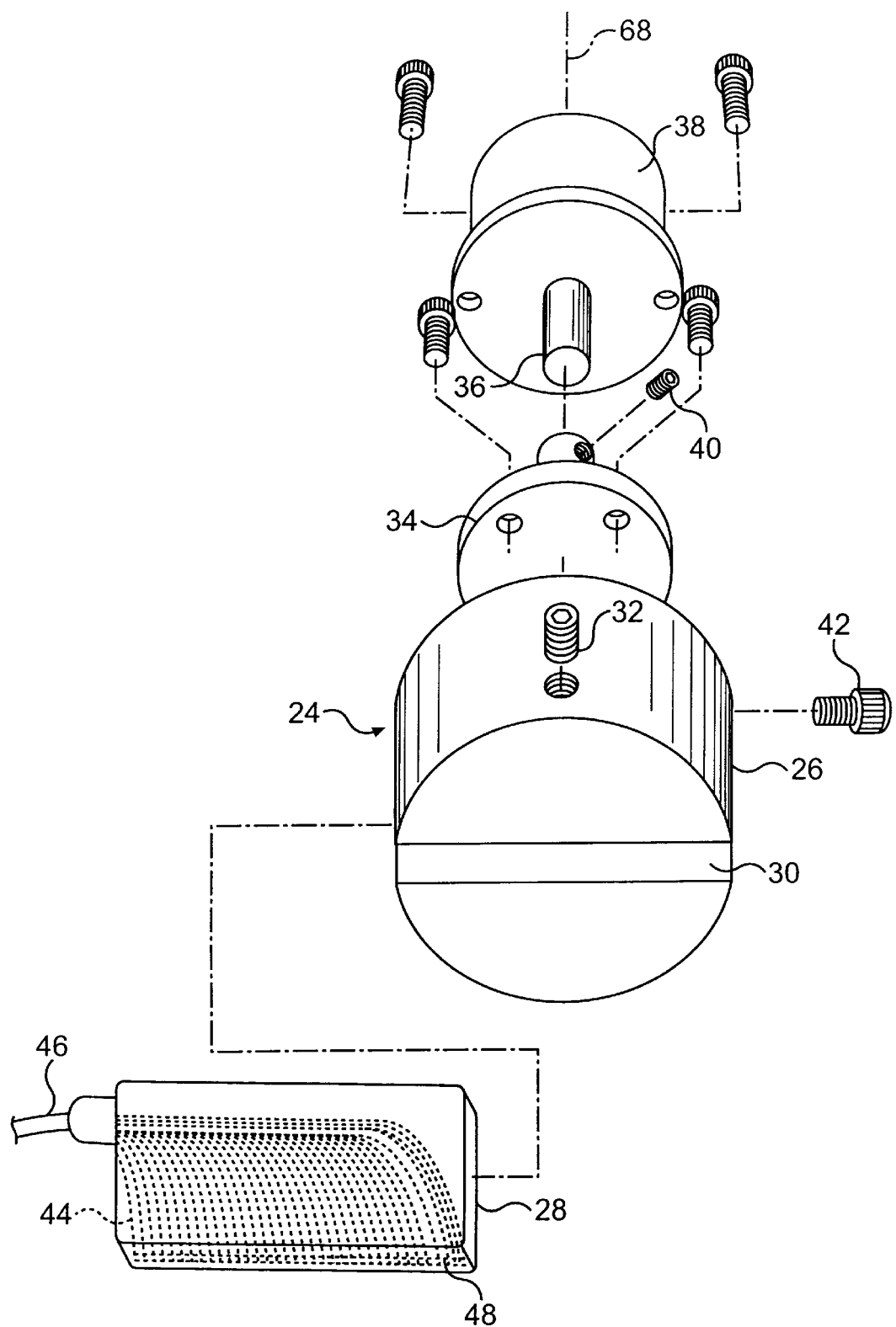
FIG. 4 is an exploded view of an embodiment of a detector device and adjusting motor for use in an optical web defect detection system constructed in accordance with the present invention.

Referring to FIG. 4, a detector 24 includes a housing 26 receiving an elongated optical sensor 28 in a slot 30. Sensor 28, for example a IR2.53S sensor available from Danner Engineering, is secured in slot 30 by a set screw 32. A hose clamp may also be used to secure the sensor. A cap 34 is mounted to the top 7 of housing 26 to receive a shaft 36 of a servo motor 38. Shaft 36 is secured in cap 34 by set screw 40 so that detector 24 rotates with shaft 36. A screw 42 is received in housing 26 so that the screw's end extends outward from the housing to act as a stop to limit rotation of the detector, as is discussed in more detail below.

Sensor 28 includes a plurality of fiber optic elements 44 supplied by a cable 46 and fanning out within the sensor so that the ends of the fiber optic element extend along the longitudinal sensor surface 48 of sensor 28.

Figure 2:
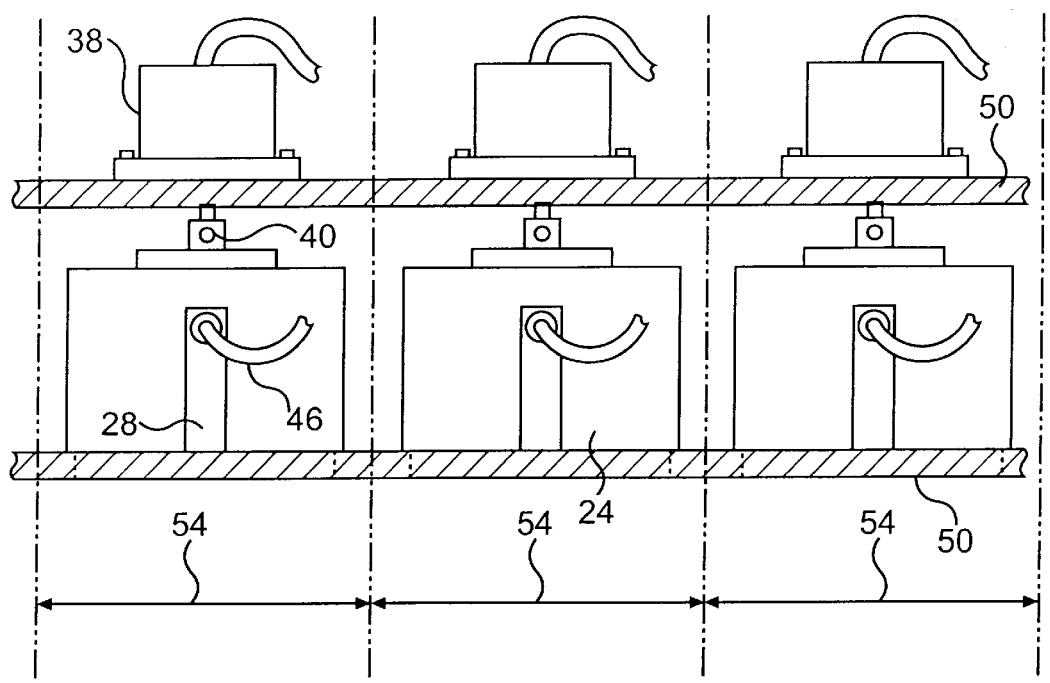
FIG. 2 is a partial plan view of the optical web defect detection system as in FIG. 1.
Figure 3:
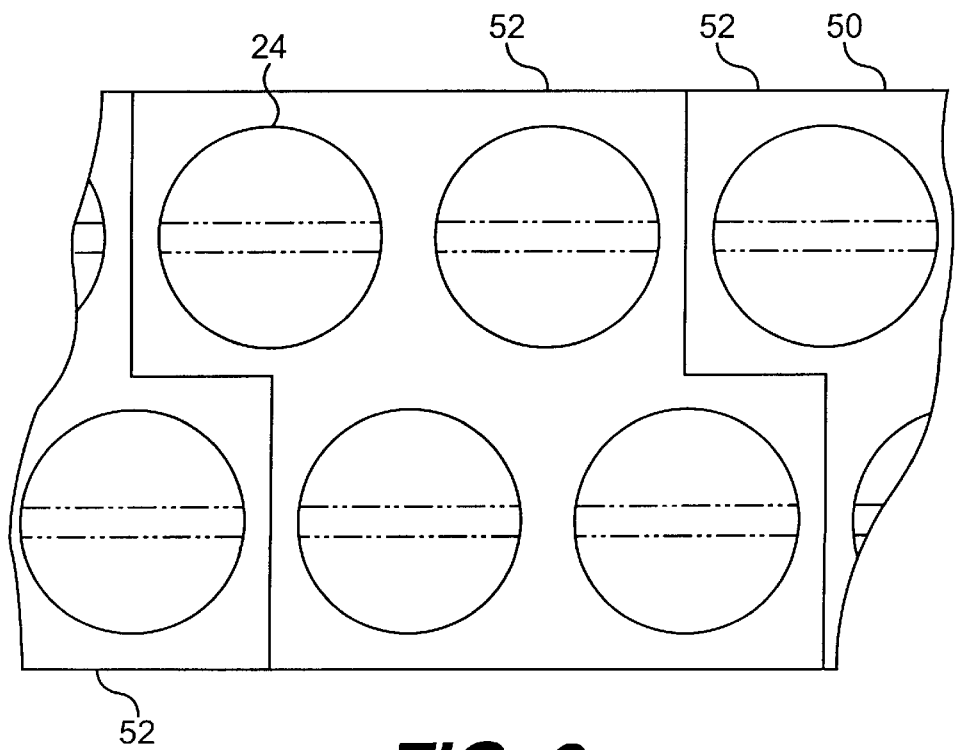
FIG. 3 is a partial bottom view of an embodiment of an optical web defect detection system constructed in accordance with the present invention.

Referring to FIGS. 1, 2 and 3, a plurality of detectors 24 are disposed in two rows in a frame 50 extending across the width of web 14. Frame 50 has a flat bottom to flatten the web passing beneath the detectors. A pair of florescent lights 52 (one of which is shown in FIG. 1) are secured to frame 12 and extend beneath web 14 beneath the respective rows. It should be understood, however, that any suitable light source, for example halogen bulbs beneath each detector, may be used. Referring to the partial bottom view of a frame 50 in FIG. 3, the detectors of one row are staggered with respect to those of the other row so that the sensor surfaces 48 receive light from the respective lights 52, modulated by web 14, across the entire width of web 14 for which it is desired to detect defects.

The frame 50 shown in FIG. 3 is constructed from frame blocks 52 each housing four detectors 24. In this manner, groups of detectors 24 may be added or subtracted from the system, depending on the width of web 14. It should be understood, however, that various suitable constructions may be provided. For example, FIG. 1 illustrates a frame 50 in which each frame block 52 houses two detectors.

As shown in FIGS. 1 and 3, each detector 24 is disposed in a transverse position in which its sensor 28 is aligned transverse to the path of travel 20 of web 14. Because of the overlapping arrangement of the detector sensor areas 48 of the parallel detector rows, the entire width of web 14 may be monitored without movement of the detectors. If the system is used to inspect a woven web having weft elements and perpendicular warp elements, this position permits the system to detect weft element defects. In particular, the sensor areas 48 are generally aligned with the weft elements, for example yarn. Thus, as web 14 moves between the detectors 24 and light elements 52, the web modulates the light from the light elements so that the sensors 48 receive a varying light signal. Specifically, each weft element substantially blocks light, whereas gaps or interfaces between adjacent weft elements permit light, or a greater amount of light, to pass.

Each warp element passes through a substantially constant position between the light elements and the detectors. Thus, although defects in the warp elements may have a slight modulating effect, the weft elements primarily modulate the light signal. Because the control mechanism in this embodiment is configured to detect web defects by monitoring the time varying light signal, the system primarily detects weft defects when the detectors are in the transverse position illustrated in FIGS. 1 and 3. It should be understood, however, that the system in the transverse arrangement may also detect warp element defects when such defects are significant enough to affect the time-varying signal detected by the transverse sensors.

To search primarily for warp element defects, detectors 24 may be rotated 90° so that detection areas 48 of sensors 28 are aligned generally with the path of travel 20 (FIG. 1) of web 14, as shown in FIG. 3. In this longitudinal position, however, the warp elements do not sequentially pass in front of the sensors as do the weft elements and, therefore, do not create a similar time-varying light signal. To create such a signal, and to permit the detectors to operatively scan the entire width of the web, frame 50 is moved back and forth a distance at least sufficient to allow the scanning area of each detector to overlap that of its adjacent detector(s) or those of the proximate detectors in the other detector row.

For example, frame 50 may be reciprocally moved so that the detectors 28 follow reciprocal paths, indicated at arrows 54, thereby allowing the detectors of a detector row to scan the width of web 14. The second detector row scans the same area as the first. Since the rows are offset with respect to each other, system reliability is increased. Alternatively, because of the double row arrangement, the distance each detector is moved may be shortened from that illustrated in FIG. 3, thereby permitting a faster cycle and increasing reliability.

Referring to FIG. 1, frame 52 is slidably disposed on rails 56 so that the frame may be moved reciprocally by a shift mechanism including a motor 58 driving a rack and pinion gear mechanism 60. Motor 58 is controlled by a control mechanism 62 which communicates with the motor by a communication line, indicated at 64. Frame 52 may be reciprocally shifted at any suitable rate, for example ten cycles per second, depending, for example, on the construction and speed of web 14. It should be understood that various suitable oscillatory mechanisms, for example a crankshaft arrangement, may be used to reciprocally shift the frame.

Since, in the illustrated embodiment, the system is arranged to primarily monitor either warp defects or weft defects, two such systems may be employed on the same machine if it is desired to simultaneously monitor for both type of defects. The detectors of one system are arranged in the transverse position, while those of the other system are arranged in the longitudinal position.

Referring again to FIG. 1, detectors 24 receive light passing through web 14 as it moves between the detectors and light elements 52. It should be understood, however, that the present invention may comprise any suitable arrangement in which one or more detectors receive light modulated by a moving web. That is, the detectors receive light with which the moving web interferes so that changes in the light received by the detectors other than the light's natural variations, indicate changes in the moving web. Accordingly, for example, the detectors may receive light that is reflected from, rather than that passes through, the moving web. Furthermore, the system may monitor any suitable light signal parameter, for example amplitude and/or frequency.

Control mechanism 62 controls each motor 38, and receives the output of sensors 28 from lines 46, over bidirectional control lines 66. Initially, where the web is comprised of weft and warp elements, control mechanism 62 controls the motors to move the detectors to either the transverse position and the longitudinal position discussed above. This may be effected by an operator controlled switch (not shown) which activates a processor of control mechanism 62 to activate appropriate relays to activate the motors. Stops (not shown) within frame 50 may be provided to engage the head of stop screw 42 (FIG. 4) of each detector 24 to restrict the detector's movement about its vertical axis 68 (FIG. 4) to slightly greater than a 90° arc, the opposite extremes of the arc being the transverse position and the longitudinal position, respectively. As explained in more detail below, the control mechanism then automatically makes fine adjustments to the detector's rotational position to align the sensor within the transverse or longitudinal position to optimize the signal received by the detector.

Figure 5:
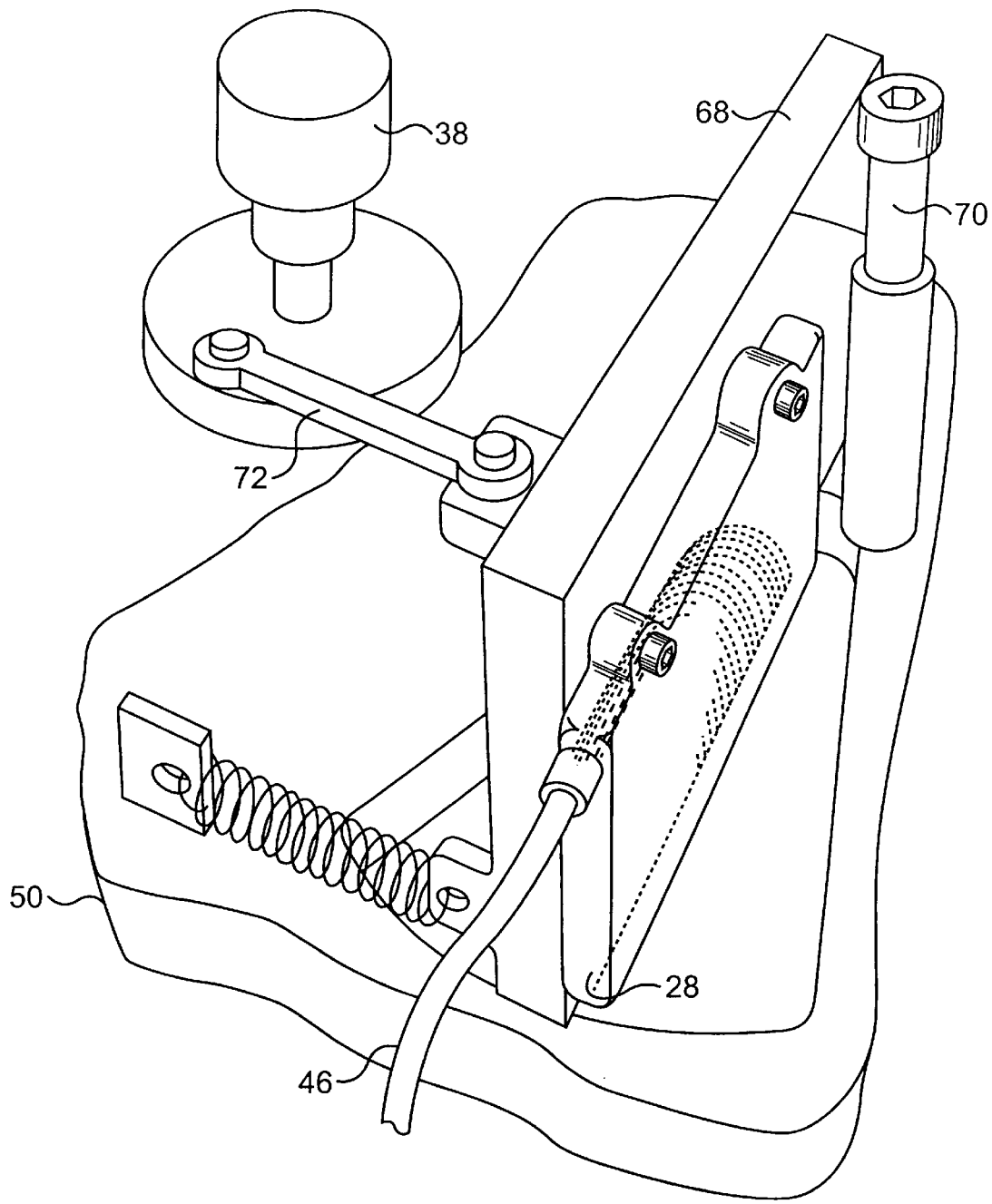
FIG. 5 is a perspective of an embodiment of a detector device and adjusting motor for use in an optical web defect detection system constructed in accordance with the present invention.

One alternate arrangement of the detectors and the adjustment mechanism is illustrated in FIG. 5. Here, frame 50 comprises a flat plate under which web 14 (FIG. 1) passes. A plurality of elongated sensors 28 are secured to respective panels 68 each pivotally mounted to frame 50 by a hinge 70. Motor 38 drives a cam mechanism 72 responsively to a control mechanism 62 (FIG. 1) to align sensor 28 to optimally receive the modulated light signal.

Figure 8:
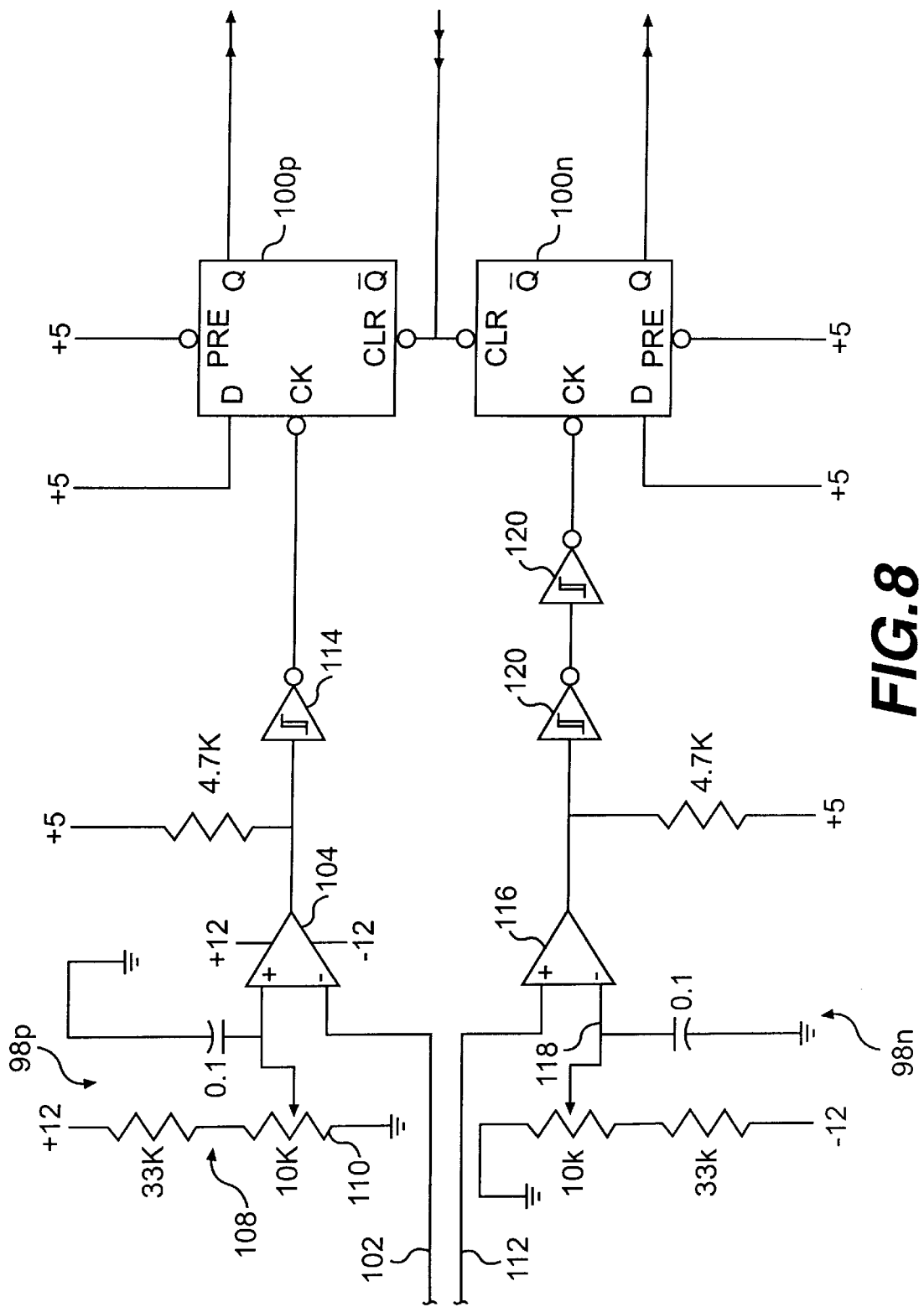
FIG. 8 is a partial schematic illustration of an embodiment of a control mechanism for use in an optical web defect detection system constructed in accordance with the present invention.
Figure 9:
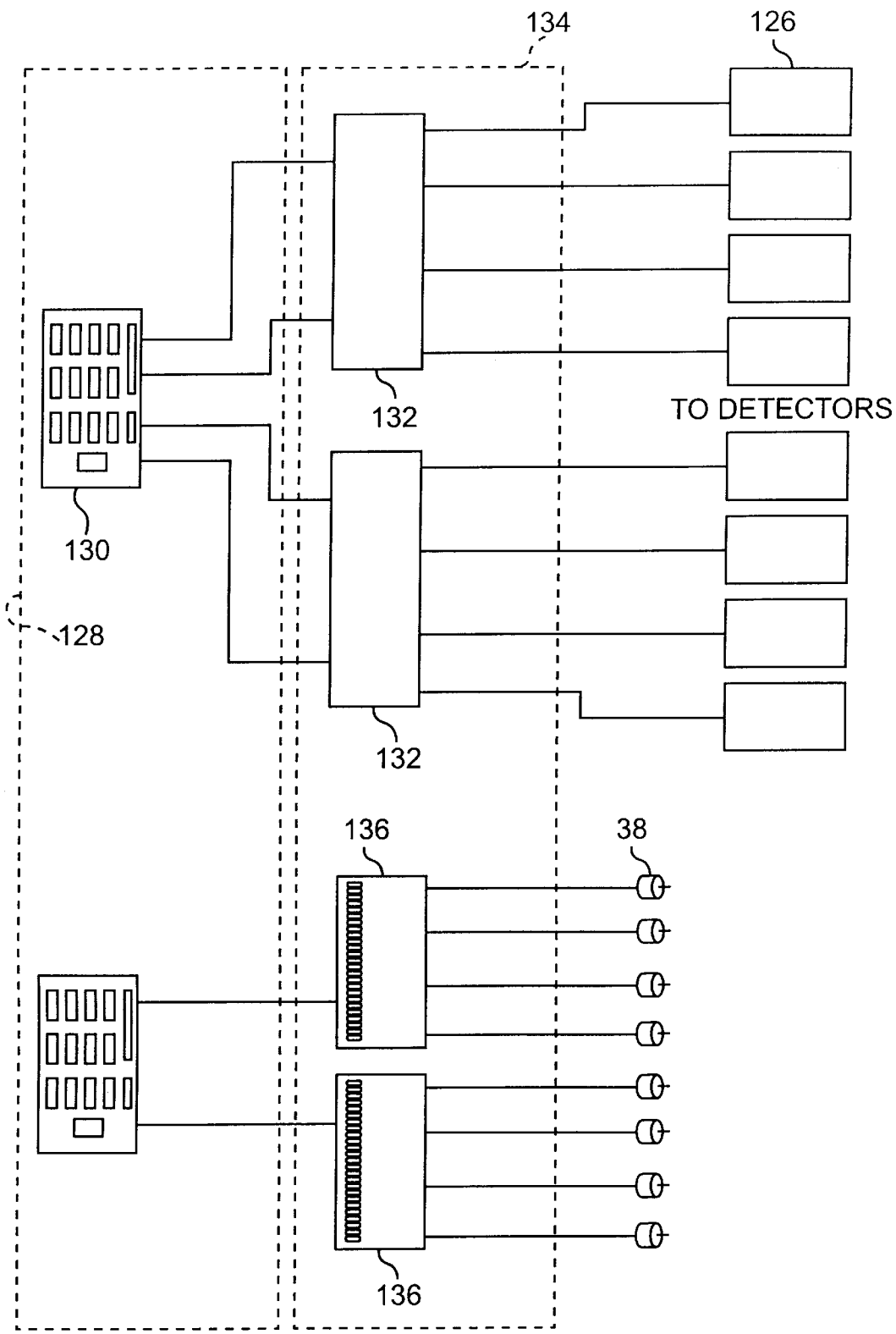
FIG. 9 is a schematic illustration of an embodiment of a control mechanism and adjustment mechanism for use in an optical web defect detection system constructed in accordance with the present invention.
Figure 10:
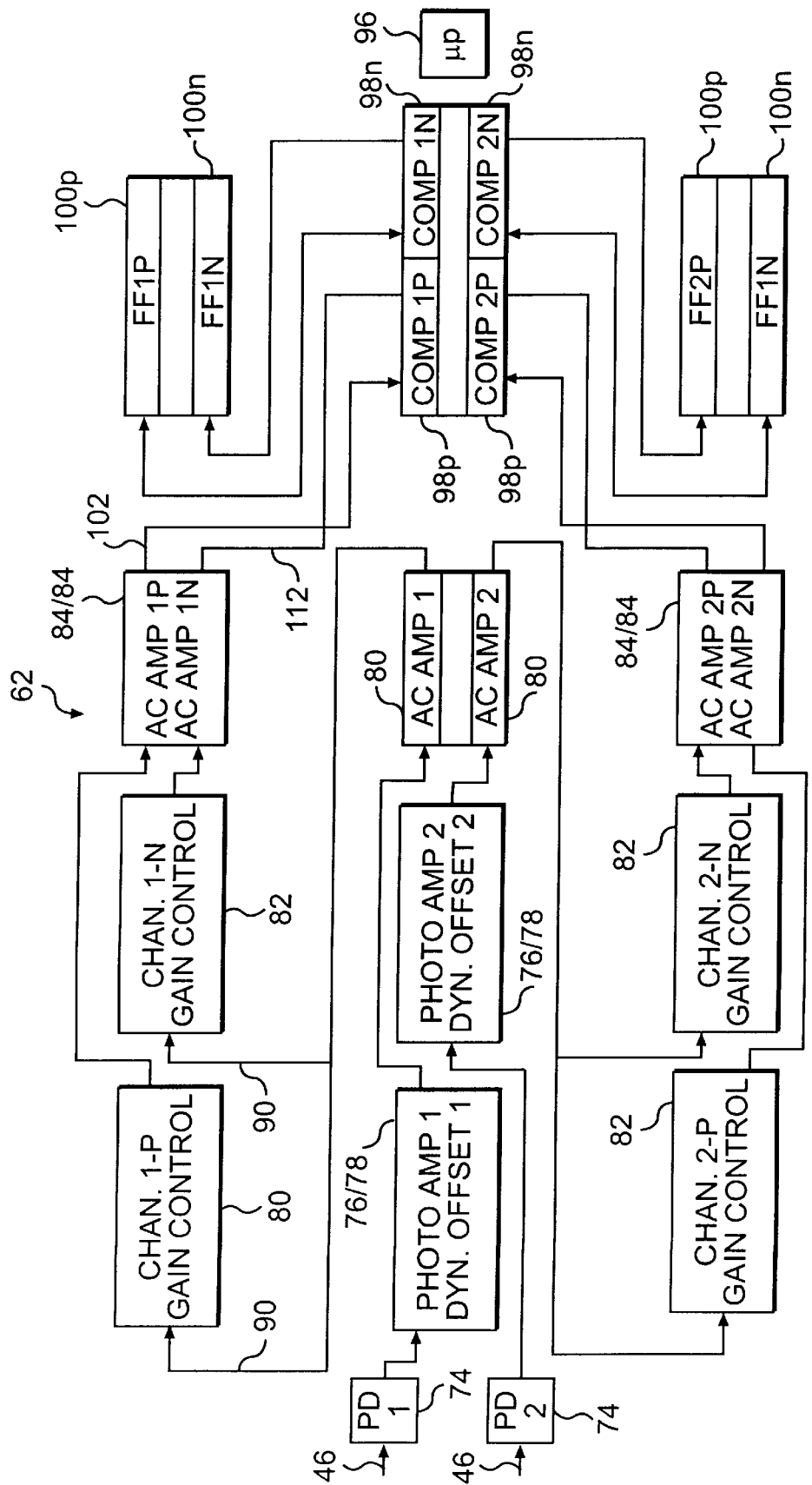
FIG. 10 is a partial block diagram of an embodiment of a control mechanism for use in an optical web defect detection system constructed in accordance with the present invention.

The control mechanism is schematically illustrated in FIGS. 6–10. Initially, FIG. 10 illustrates a control system having a gain stage and a comparator stage for each of two detectors. Each gain stage includes a photoamplifier 76, a dynamic offset 78, a first AC amplifier 80, two adjustable gain control devices 82 and two second AC amplifiers 84. Each comparator stage includes a pair of comparators 98p and 98n and a pair of flip-flops 100p and 100n. It should be understood that this architecture may be repeated for any number of detectors.

Figure 6:
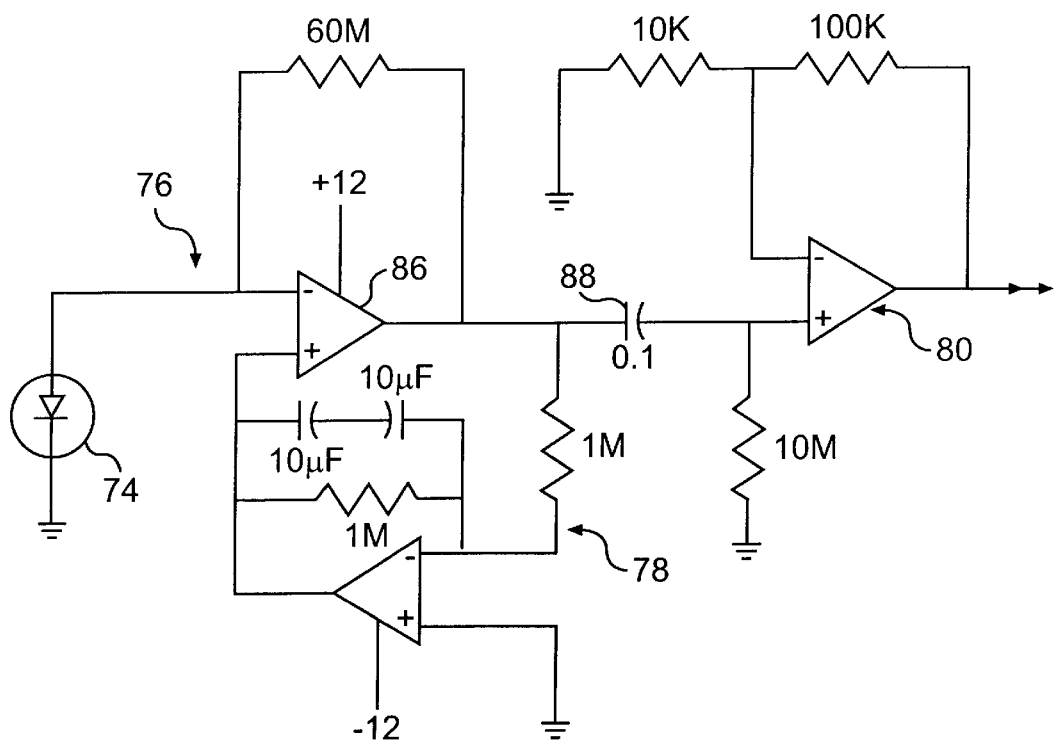
FIG. 6 is a partial schematic illustration of an embodiment of a control mechanism for use in an optical web defect detection system constructed in accordance with the present invention.

Referring also to FIG. 6, each fiber optic bundle 46 feeds to a photodiode 74, which is preferably a sensitive, low noise device, for example a 53374 silicon detector available from Edmund Scientific. Although photodiodes may be preferred in certain circumstances for cost, speed and sensitivity, it should be understood that other devices, such as CCD cameras or line scan cameras, may be used instead of the photodiode. Furthermore, a lens and line scan chip may be mounted on the detector in place of the fiber optic sensor.

The output from diode 74 is directed to op amp 86 which is arranged as a transresistance amplifier. To remove DC signal components and low frequency ambient light variations, for example due to changes in web style or density or to aging of the light elements, dynamic offset circuit 78 feeds back the amplifier output. Dynamic offset circuit 78 operates under an approximately one second time constant, causing the op amp to subtract DC components and low-frequency light changes from the photodiode output. Accordingly, the output of amplifier 86 is approximately equal to the AC component of the photodiode output.

As noted above, the light signal reaching the fiber optic detector is at a minimum when a web element passes directly beneath the sensor and is at a maximum as a gap or interface between adjacent elements passes beneath the sensor. The result is the same whether the detectors are in the transverse position, where the weft elements pass beneath the sensors, or in the longitudinal position, where the detectors are moved reciprocally over the warp elements. Since the dynamic offset circuit removes DC and low frequency AC components from the photodiode output, the output of amplifier 86 is that part of the photodiode output corresponding to the modulated light signal from the web and amplified by the transresistance amplifier gain. Capacitor 88 removes any remaining DC component, and the signal output to AC amplifier 80 is a time-varying signal having negative and positive components corresponding to the passage of web elements and the gaps or interfaces therebetween, respectively, under the sensor.

Figure 7:
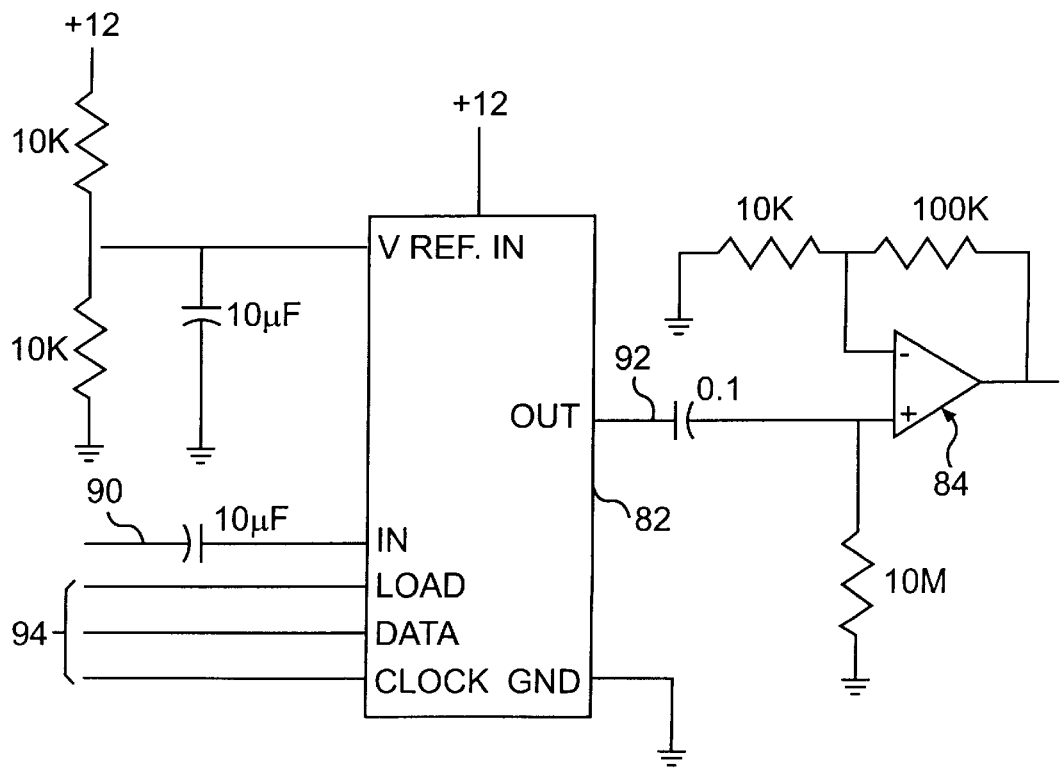
FIG. 7 is a partial schematic illustration of an embodiment of a control mechanism for use in an optical web defect detection system constructed in accordance with the present invention.

AC amplifier 80 amplifies this time-varying signal by a factor of ten, outputting the amplified signal to the input 90 of adjustable gain device 82 as shown in FIG. 7. While FIG. 10 illustrates two adjustable gain control devices and AC amplifiers per detector, the construction and arrangement of each such pair is identical. For purposes of clarity, therefore, FIG. 7 illustrates only one pair.

In the illustrated embodiment, adjustable gain device 82 is an attenuator which receives input 90 and outputs a signal at 92 attenuated by a factor determined by the setting of control lines 94. AC amplifier 84 is identical to amplifier 80, again amplifying its input signal by a factor of ten.

Referring again to FIG. 10, signal 90 is directed to separate channels, each having an attenuator 82 and amplifier 84. This allows separate analysis of the output of amplifier 80 for positive and negative deviations. Accordingly, each block following amplifier 80 is identified as "P" or "N" to identify the block as part of the "positive" or "negative" channel. As is explained in more detail below, this permits the microprocessor 96 to separately control the positive and negative attenuators 82 so that the system accurately detects defects based on positive and negative signal variations.

The outputs of the positive and negative amplifiers 84 are directed to the comparator stage comprising "positive" comparator circuit 98p, "negative" comparator circuit 98n, "positive" flip-flop 100p and "negative" flip-flop 100n. Referring also to FIG. 8, the output 102 from the positive amplifier 84 is input to a comparator 104, which compares the signal to a predetermined voltage at 106. In the illustrated embodiment, voltage 106 is determined by a voltage divider network 108 including a variable resistor 110. It should be understood, however, that this voltage is a reference voltage which might not require adjustment and that the circuit may therefore be arranged so that voltage 106 is invariable.

As shown in FIG. 8, reference voltage 106 is approximately 3 volts. The particular voltage used, however, may depend on the operating range of the components in the upstream circuitry. In particular, the output 102 and 112 of the positive and negative amplifiers 84 (FIG. 10) is generally between approximately −3 and +3 volts.

Comparator 104 goes low whenever the signal on line 102 exceeds the voltage at 106. An inverting Schmitt trigger 114 changes this to a positive signal which is input to flip-flop 100p. When inverter 114 changes state, flip-flop 100p output Q becomes equal to input D, here set to positive five volts. Output Q is directed to microprocessor 96 (FIG. 10), thereby allowing the microprocessor to monitor when the signal at 102 exceeds the reference voltage. That is, the microprocessor monitors, by the gain and comparator stages of the control mechanism, a signal corresponding to the modulated light signal received from the moving web to determine when that signal exceeds a predetermined reference level.

To calibrate the control system so that the reference voltage at 106 may be used to determine when a defect has occurred, the microprocessor automatically adjusts the gain of attenuator 82 (FIG. 7). At start-up, for example, the microprocessor sets control lines 94 so that the attenuator is set to its lowest attenuation level. Accordingly, the gain stage is set to its highest gain level. At this point, the positive peak of the signal on line 102 should exceed the reference voltage at 106 (FIG. 8), thereby causing the Q output of flip-flop 100p to change state. In response, the microprocessor clears the flip-flop and increases the attenuation of attenuator 82 by appropriate signals over the control lines. The microprocessor continues this process, clearing the flip-flop approximately ten times per second and increasing the attenuation of the attenuator at approximately 1 dB steps until flip-flop 100p (FIG. 8) fails to change state.

At the end of this first calibration stage, any increase in the positive peak of the modulated light signal from the web causes flip-flop 100p to change state. From experience, however, it may be determined that an increase of a certain percentage above this level indicates a defect, for example a mispick or a thin place, that justifies notification of an operator. Accordingly, in a second calibration stage, microprocessor 96 (FIG. 10) further steps the attenuation level of the attenuator so that the peak of the signal on line 102 must exceed its normal value by this percentage before flip-flop 100p is triggered. Following this self-calibration, therefore, a change of state of flip-flop 100p notifies the microprocessor that a defect has occurred, permitting microprocessor to initiate notification of an operator, as discussed in more detail below.

Referring again to FIGS. 8 and 10, a similar arrangement of comparator circuit 98n and flip-flop 100n provides notification of defects through analysis of the amplifier 84 output from line 112. Specifically, the amplifier output on line 112 is compared by a comparator 116 to a negative reference voltage at 118 (approximately −3 volts in the illustrated embodiment) so that comparator 116 goes high when ever the amplifier output on line 112 drops below this voltage. A pair of inverting Schmitt triggers 120 is provided to assure a clean transition of the signal as it is directed to flip-flop 100n.

Microprocessor 96 calibrates the negative channel as it calibrates the positive channel, simultaneously resetting the flip-flop 100p and 100n and simultaneously stepping each attenuator until the first of the flip-flops stops triggering. The microprocessor continues stepping the attenuator for the other channel until its flip-flop also ceases to trigger. Ideally, however, both flip-flops should become stable at approximately the same time.

Defects, such as double picks or over-thick web elements, that tend to increase the negative peak may have a greater or lesser effect on the negative signal peak than positive-related defects, such as mispicks, have on the positive signal peak. Thus, the microprocessor may be programmed to set different final attenuation levels for the positive channel attenuator and the negative channel attenuator.

Once the system detects a defect, the microprocessor activates an alarm mechanism, for example a dye spray nozzle 122 over a communication line 124 (FIG. 1), which marks the selvage proximate the defect. The dye mark may be mechanically or visually detected so that this portion of the web may be removed prior to finishing or sale. Other alarm mechanisms may include, for example, audible or visual alarms or machine controls to automatically stop the machine.

FIG. 9 illustrates a block diagram of the hardware components of control mechanism 62. The gain stage and comparator stage for each detector are constructed on respective circuit boards 126. Accordingly, the arrangement illustrated in FIG. 9 accommodates eight detectors. Depending on the components used, however, multiple gain and comparator stages may be mounted on a single board. For example, if the configuration of FIG. 10 is mounted on a single board 126, the arrangement of FIG. 9 accommodates sixteen detectors. Input/output cards 130 plug into a PC 128 to allow boards 126 to communicate with the microprocessor through termination boards 132 of an input/output cabinet 134.

The microprocessor may be housed in any conventional computing device, for example a custom built system including a microprocessor and various memory and input/output devices. Furthermore, however, the system may employ a conventional personal computer 128 having standard input/output ports and operating systems. Regardless of the platform, those of ordinary skill in the art should understand that the computing device may be programmed so that the microprocessor is able to execute the functions described above.

The microprocessor also controls servo motors, for example unipolar stepper motors, 38 through relay modules 136. For example, simultaneously with the first self-calibration of the control mechanism described above, the rotational position of the detectors is automatically calibrated to maximize the signal strength received by the detectors. More specifically, as the system steps through the attenuation levels to determine when the flip-flops stop triggering, it uses this information to simultaneously calibrate the detector position.

In one embodiment, the microprocessor calibrates the rotational position of each detector by monitoring the output of its respective flip-flop 100p (FIG. 8). Assuming that the detector is in either the longitudinal or the transverse position, each detector is initially positioned at an extreme end of its 90° arc, and its positive channel attenuator is set to its lowest attenuation level. That is, the positive channel gain is set to the highest level. With the web running underneath the detectors, each positive channel attenuator is stepped through increasing attenuation levels until the positive channel flip-flop ceases to trigger. This is the first stage of the control mechanism calibration discussed above. At this point, the control mechanism rotates the detector's motor 38 about axis 68 (FIG. 4) by a predetermined increment, for example 0.9°.

If the modulated light's signal strength is higher at this position, the positive flip-flop triggers, and the attenuator is again stepped to higher attenuation levels until the flip-flop again ceases to trigger. If the flip-flop doesn't trigger at the new position, the motor is incremented again, and the process is repeated through a predetermined range of rotation of the motor, for example approximately 18°. At the completion of this arc, the detector is returned to the last position at which the positive flip-flop triggered. This is the position at which the detector received the strongest modulated light signal with respect to the positive peak. Accordingly, the position of the detector has been adjusted to optimize reception of the modulated light, in this case with respect to the positive signal portion.

Accordingly, when the system simultaneously calibrates the control mechanism and the detector position, the process of stepping through attenuation levels until the flip-flop becomes stable is repeated at incremental detector positions. This extends the first calibration stage of the control mechanism. Following this stage, as described above, the microprocessor sets the final attenuation level for the positive channel and negative channel attenuators, and the system searches for web defects.

Control mechanism self-calibration may occur repeatedly during machine operation, for example periodically or intermittently after start-up, and/or at changes of the web. Calibration subsequent to start-up may or may not include detector position self-calibration, depending on the needs of the operator or the requirements of a particular configuration.

In another preferred embodiment, the detector position calibration is independent of the control mechanism calibration. In this embodiment, an analog-to-digital converter samples the AC signal corresponding to the modulated light signal at some point in the gain stage, for example following amplifiers 76, 80 or 84 (FIGS. 6 and 7), and outputs to the microprocessor a digital signal corresponding to the AC component of the modulated light signal. As before, the detector begins at one extreme of its 90° rotational arc, depending on whether the detector is in the transverse or the longitudinal position. If the converter samples the signal upstream from the attenuator, the attenuator setting is unimportant. If the converter samples the signal downstream from the attenuator, however, the attentuator setting is maintained at an arbitrary level. The detector is then incrementally rotated through a predetermined arc, for example 18°, while the microprocessor measures the positive signal peak at each step. At the end of the arc, the detector is returned to the position at which the highest peak was measured.

Each detector position calibration method described above is based on the positive signal peak. It should be understood, however, that either method may base the calibration on the negative peak, for example by monitoring the output of the negative channel flip-flop or by monitoring the negative peak from the analog-to-digital converter. Furthermore, the system may monitor both the positive and negative signal portions and determine the appropriate position for the detector based on the greatest signal magnitude.

Figure 11:
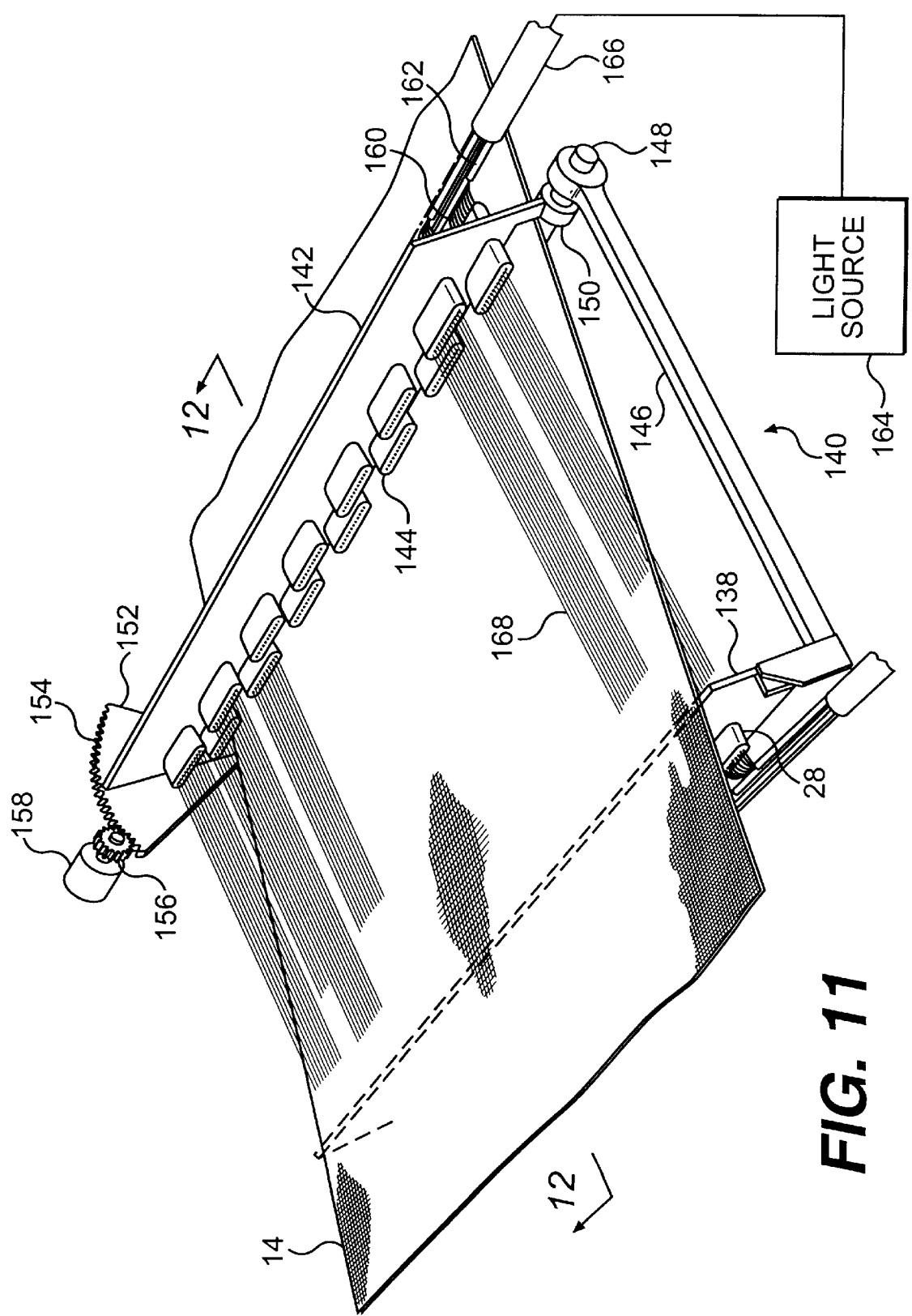
FIG. 11 is a perspective view of an embodiment of an optical web defect detection system constructed in accordance with the present invention.

In a further embodiment of the invention illustrated in FIG. 11, the detectors comprise sensors 28 disposed in a plate 138 extending transversely across web 14. Plate 138 is part of a frame 140 that also includes a plate 142 in which light emitters 144 are disposed. In a preferred embodiment, sensors 28 and light emitters 144 are identical fiber optic devices (for example Danner Engineering IR2.53S sensors), differing in the devices to which they are connected. The fiber optic elements from each sensor 28 output to a control system having a dual-channel gain stage and comparator stage as described above with respect to FIG. 10. In contrast, each emitter 144 includes a plurality of fiber optic elements 160 that bundle to a cable 162 that, in turn, passes through a conduit 166 to a light source 164. Light source 164 may be any suitable light source, for example a lamp, capable of directing light to the fiber optic cables and thereby to the light emitters. The application of light signals to fiber optic cables and elements should be well understood in this art and is therefore not discussed in further detail herein.

Two rigid arms 146 (one of which is shown in FIG. 11) extend from either side of plate 138 to attach to a pin 148. Plate 142 is rotatably attached to pin 148 by two annular rings 150 (one of which is shown in FIG. 11) at either end of the plate. Arms 146 are fixed to pin 148 so that they, plate 138 and pin 148 rotate together. A bracket fixed to one end of plate 142 has an arcuate edge that defines teeth 154 that in turn cooperate with a drive wheel 156 of a motor 158.

Figure 12:
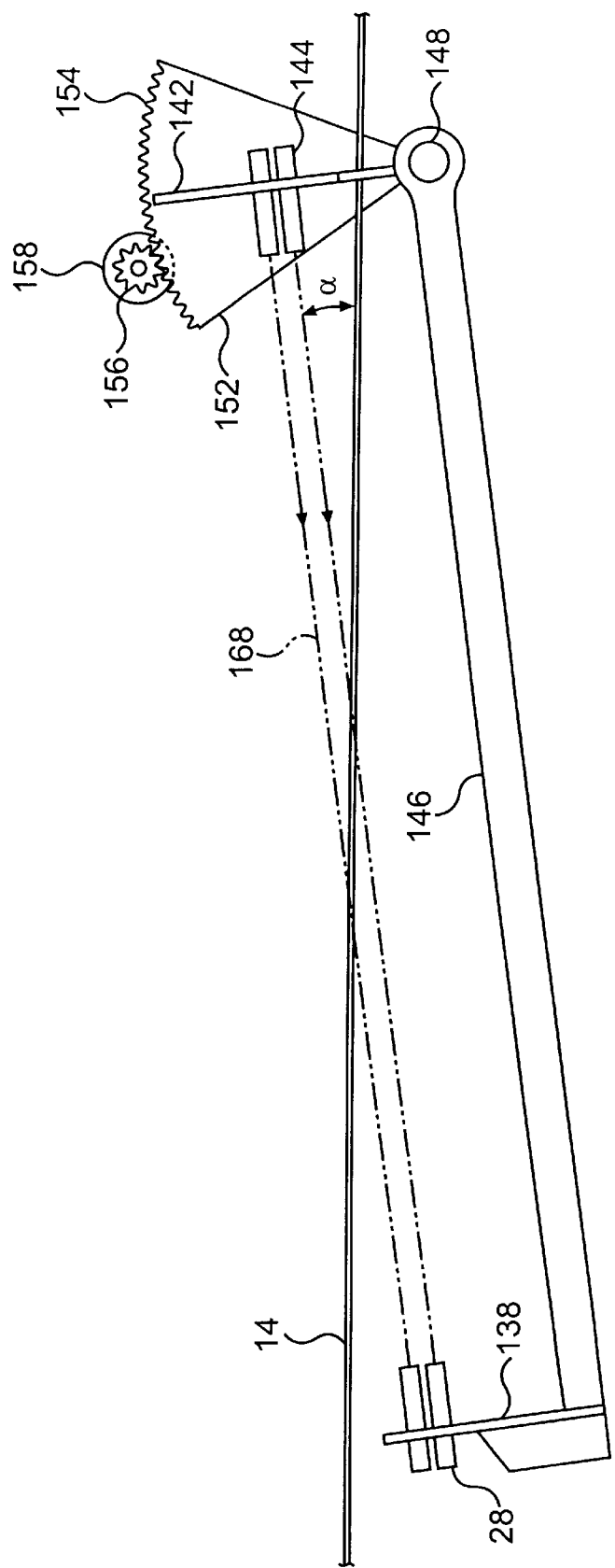
FIG. 12 is a plan view of the system as in FIG. 11.

Referring also to FIG. 12, plates 138 and 142 are parallel to each other, and the plates hold sensors 28 and light emitters 144 perpendicularly to each other. Thus, the front faces of sensors 28 and emitters 144 directly oppose each other on opposite sides of web 14. Fiber optic elements 160 fan out to the end surfaces of their respect light emitters 144. Thus, the emitters output light 168 to web 14 at an angle a with respect to a plane defined by the web.

Light 168 is not collimated in the illustrated embodiment. Thus, angle α is measured between the web and the path of light from the emitter that is modulated by the web and thereafter received by an opposing sensor 28. The particular emitters 144 shown in FIGS. 11 and 12 may be replaced by any suitable light source, for example a florescent tube that emits light in all directions.

Figure 13:
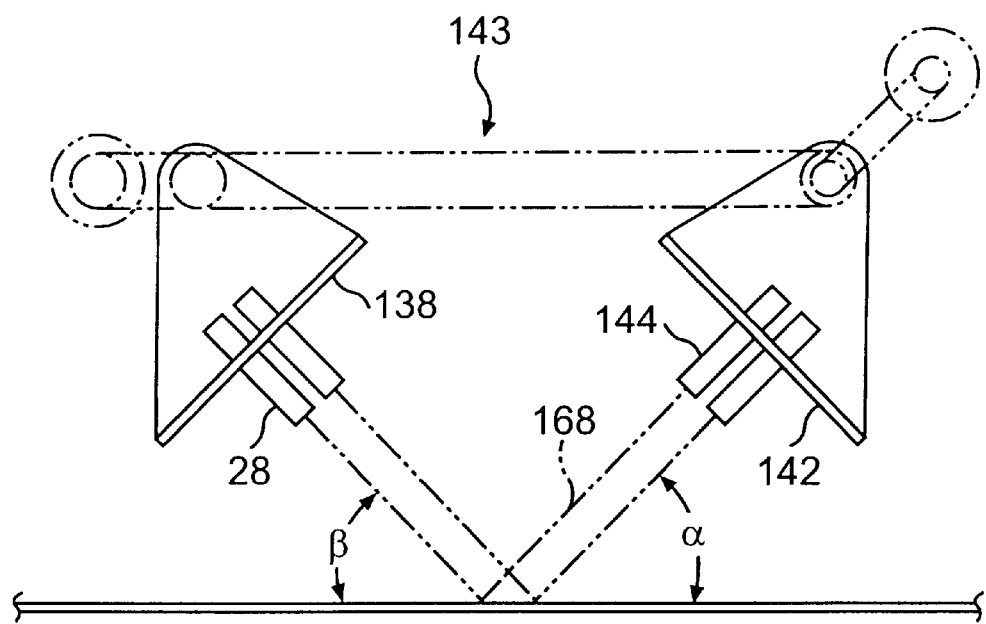
FIG. 13 is a partial plan view of an embodiment of an optical web defect detection system constructed in accordance with the present invention.

As shown in FIGS. 11 and 12, sensors 28 and emitters 144 are disposed facing each other on opposite sides of the web, and light 168 passes in a straight line from the emitters to the detectors through the web. It may be desirable in some embodiments, however, to place the emitters and sensors on the same side of the web. This is particularly true when web 14 has a multi-layer construction, as in knits or denim, that would significantly or completely block the passage of light through the web. As shown in FIG. 13, for example, sensors 28 may be disposed so that they detect light 168 from emitters 144 reflected from the web. Here, a is measured between web 14 and the emitter light that is thereafter reflected up to the detectors. Plates 138 and 142 in FIG. 13 may be pivotally attached to frame 12 (FIG. 1) and may be connected to each other through a drive 143 having suitable gearing and/or belts so that adjustment of one plate causes a corresponding adjustment of the other plate. The plates may, however, be attached to the frame so that they pivot independently of each other.

It should be understood that web 14 is not a smooth surface and that the sensors may be disposed in various positions with respect to the web depending on factors such as the material forming web 14 and the defects for which the system is monitoring. Thus, angle β is not necessarily equal to angle α. In an embodiment discussed below, for example, a sensor is disposed adjacent to an emitter so that the sensor detects light reflected back from the web. In this case as well, angle α is measured between the web and the line of incidence of the light from the emitters that is thereafter reflected back to the sensors.

It should also be understood for purposes of this discussion that web 14 is generally planar, even though it may have slight irregularities and may fluctuate as it travels along the frame.

It has been determined that disposing the sensors and emitters so that α is acute may increase the system's ability to detect defects, depending upon factors such as the web's material and rate of movement. For example, where web 14 is a polymer extrusion, an α of approximately 15° (+/−5°) increases the system's sensitivity to slight extrusion irregularities known as "chatter." The angle may vary, however, with other web materials and constructions. As discussed in more detail below, for example, an approximately 45° angle (+/−5°) may be appropriate for some woven webs.

For a given system, α may be determined by trial and error. For example, referring to FIG. 12, an operator may set α to an initial value, for example 15° or 45°, and then vary the angle while running the web to determine a particular setting that provides suitable performance.

In the embodiment of FIG. 12, α may be adjusted through operation of motor 158. From the perspective shown in the figure, rotation of drive wheel 156 in a clockwise direction increases α. Counterclockwise rotation decreases the angle.

Referring again to FIG. 11, emitters 144 are disposed on plate 142 in two rows so that the emitters in one row overlap gaps between emitters in the other. Sensors 28 are disposed in plate 138 in a corresponding pattern, and the sensors and emitters thereby monitor the entire width of web 14. This configuration is particularly suited to detect defects, such as weft defects and chatter, that occur transversely to the web's moving direction. To detect longitudinal defects, the emitters and sensors may be disposed within their respective plates so that they are rotatable by 90°. For example, each sensor and emitter may be secured in a circular bracket held in the plate by a groove so that the bracket is rotatable in the plate. Suitable stops may be provided on the bracket and on the plate to limit the rotation to a 90° so that the sensor or emitter may be aligned transversely or longitudinally with respect to the web. The entire frame 140 may then be mounted on a suitable shift mechanism, for example as shown in FIG. 1, to reciprocally shift the sensors transversely over web 14 to detect longitudinal defects in the web. In an alternate embodiment discussed below, a single longitudinally aligned sensor/emitter pair may be mounted on a carriage that moves reciprocally across the web.

Figure 14:
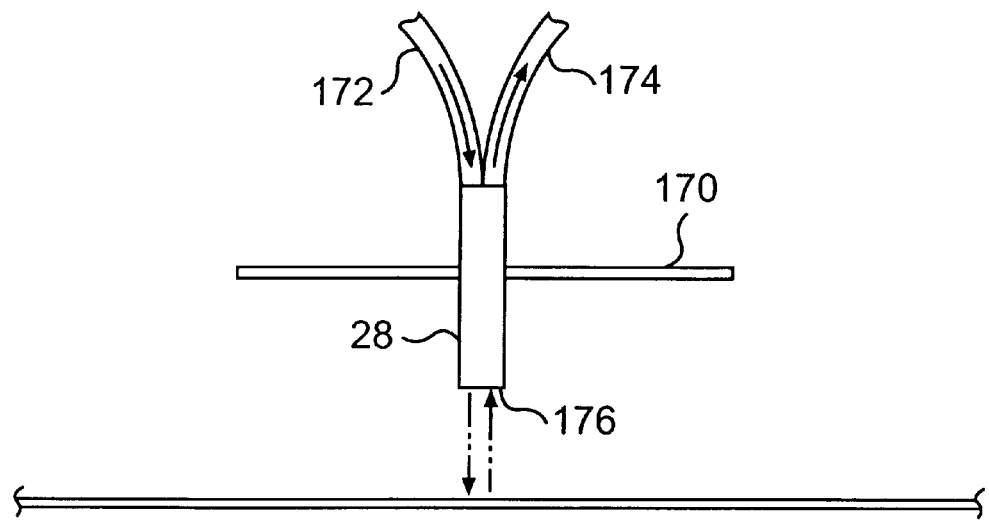
FIG. 14 is a partial plan view of an embodiment of an optical web defect detection system constructed in accordance with the present invention.

As discussed above, the sensors and light emitters may take various suitable forms. In FIG. 14, for example, an elongated fiber optic sensor 28 held in a frame 170 includes a plurality of fanned-out fiber optic elements grouped into two cables, 172 and 174, instead of one. Cable 172 is in communication with a light source so that its fiber optic elements emit light from the sensor's front surface 176. The fiber optic elements from cable 174 communicate with a downstream control system. Thus, the sensor is both the emitter and the detector. The use of these sensors may be preferable on machines such as looms where space is limited. An exemplary bifurcated fiber optic device is the P/N 20498 available from Danner Engineering.

Figure 15:
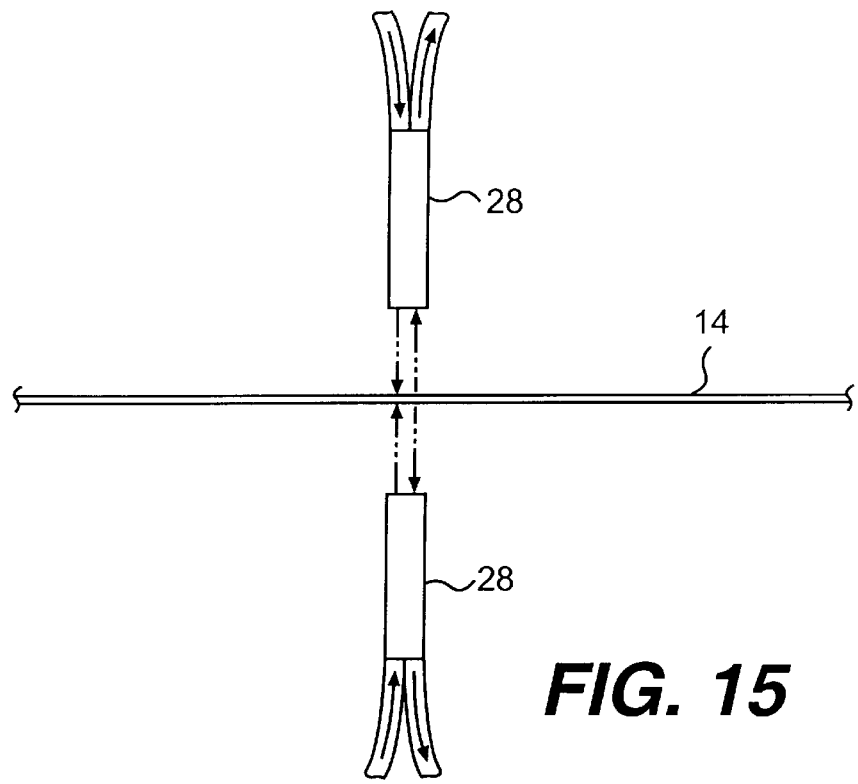
FIG. 15 is a partial plan view of an embodiment of an optical web defect detection system constructed in accordance with the present invention.

Moreover, the emitters and sensors may be disposed in various relationships to each other. Referring to FIG. 15, two bifurcated sensors 28 are disposed on opposite sides of the web 14. Thus, each sensor receives a light signal that includes its own light reflected by the web as well as light passed through the web from the other sensor.

Figure 16:
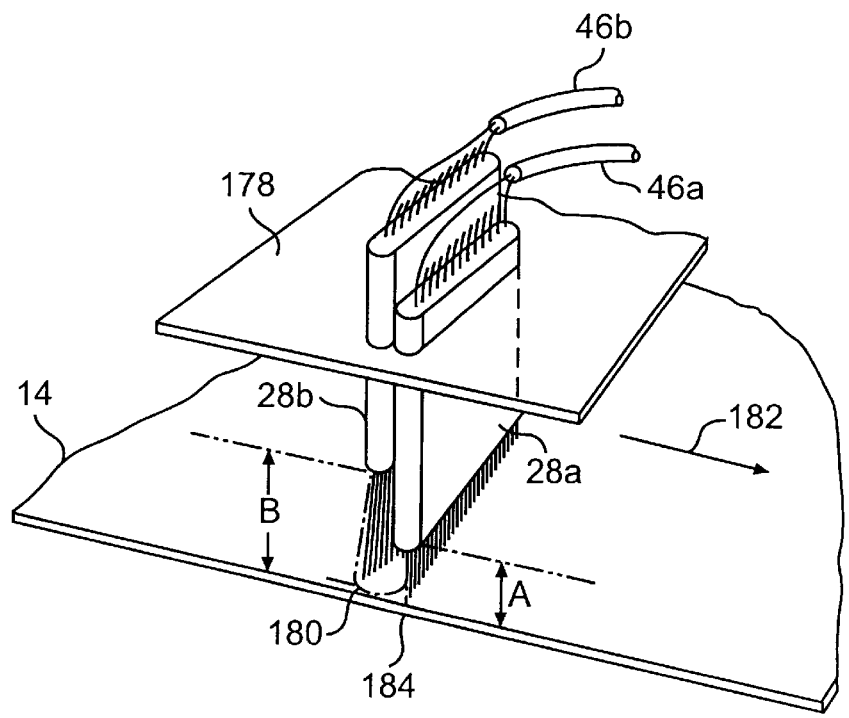
FIG. 16 is a partial perspective view of an embodiment of an optical web defect detection system constructed in accordance with the present invention.

In an arrangement illustrated in FIG. 16, a plate 178 secures two sensors 28a and 28b disposed at distances A and B above web 14. The sensors may be the same fiber optic devices as discussed above. A light source (not shown) is disposed below the web so that light from the light source passing through the web is received by the sensors. Because of its greater height above the web, detector 28b receives light from a web area 180 having a greater width with respect to the web's moving direction 182 than an area 184 from which sensor 28a receives light. In the illustrated embodiment, each of the sensors 28a and 28b is in communication with a respective control system as discussed above with respect to FIG. 10 through output cables 46a and 46b.

Because the width of area 184 is relatively narrow, narrow defects such as stop marks passing below the sensor nevertheless significantly affect the light passing through area 184. Thus, the change in the output signal from sensor 28a is large enough so that the downstream control mechanism indicates that a defect has occurred.

As should be understood in this art, stop marks extend transversely across the web. They occur where the web has contacted part of the web handling system when the web is stopped. Often, these marks are initially invisible to human operators but become apparent upon dying.

Sensor 28a might not be as effective in detecting broader, more gradual defects such as brush marks. The dynamic offset circuit discussed above with respect to FIG. 6 may tend to filter out such defects. The greater width of area 180, however, ensures that the gradual transition of a brush mark creates a sufficient transition within the area to trigger detection.

Distances of A and B may vary depending upon the web's construction, materials and speed. Thus, the particular offsets may be determined by trial and error. In a preferred embodiment, the sensors are disposed so that the system is able to detect defects by sensor 28a that it is unable to detect by the other. In this embodiment, "unable" can mean that the system would fail to detect more than 2% of such defects. Similarly, distance B is set so that the system would detect defects undetectable through sensor 28a.

Figure 17:
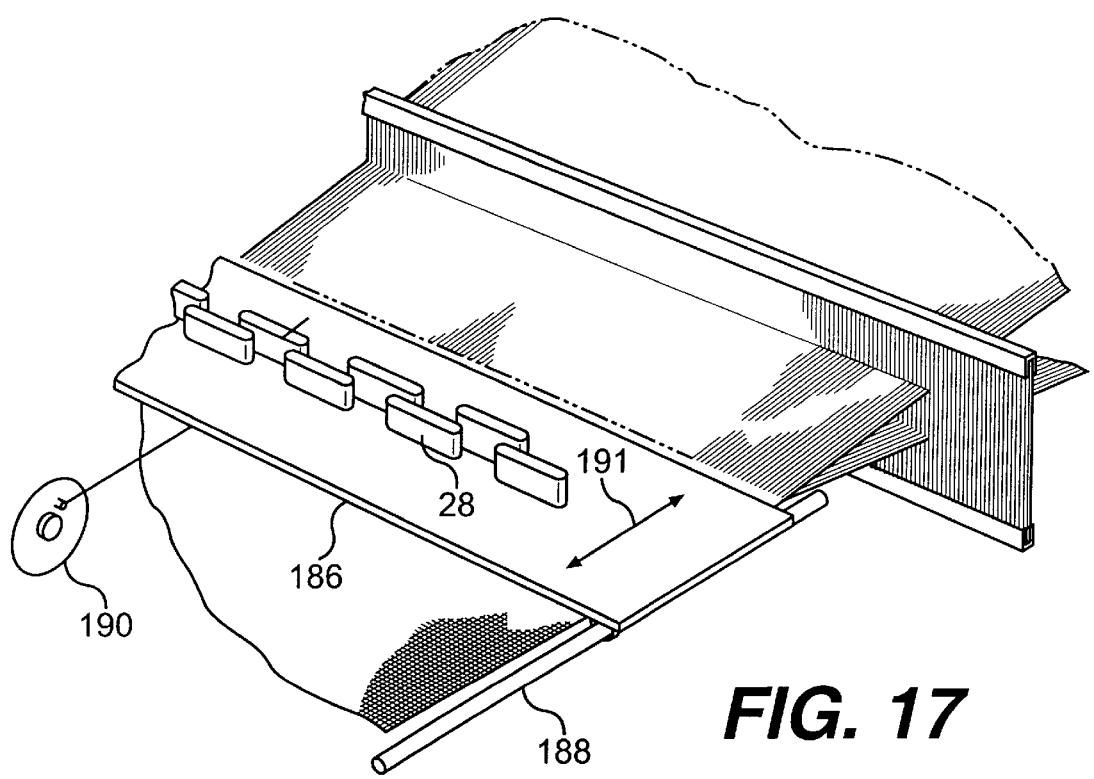
FIG. 17 is a partial perspective view of an embodiment of an optical web defect detection system constructed in accordance with the present invention.

In certain systems, for example looms, the web moves at a relatively slow speed. Thus, even where the sensors are aligned to detect transverse defects, it may be desirable to longitudinally shift the sensors to increase the relative movement between them and the web. Referring to FIG. 17, for example, a plurality of sensors 28 are held in a plate 186 slidably attached to a pair of rails 188 (one of which is shown in FIG. 17). A motor (not shown) rotates a wheel 190 schematically illustrated in FIG. 17 that reciprocally drives plate 186 on rails 188 as indicated by arrow 191. On a typical loom, the plate in the illustrated embodiment may move at approximately 1 meter per second.

Figure 18:
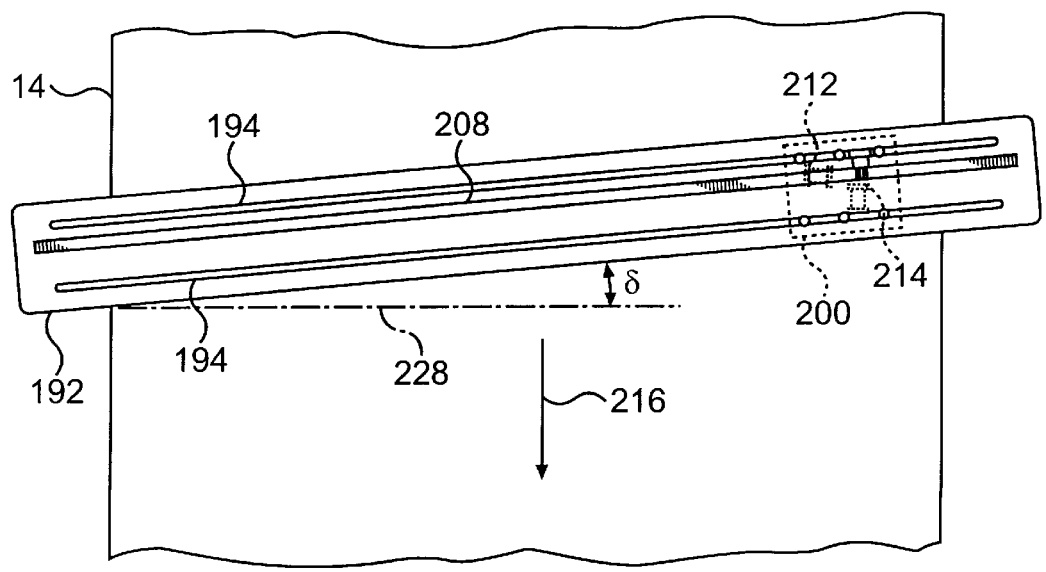
FIG. 18 is a partial top view of an embodiment of an optical web defect detection system constructed in accordance with the present invention.
Figure 19A:
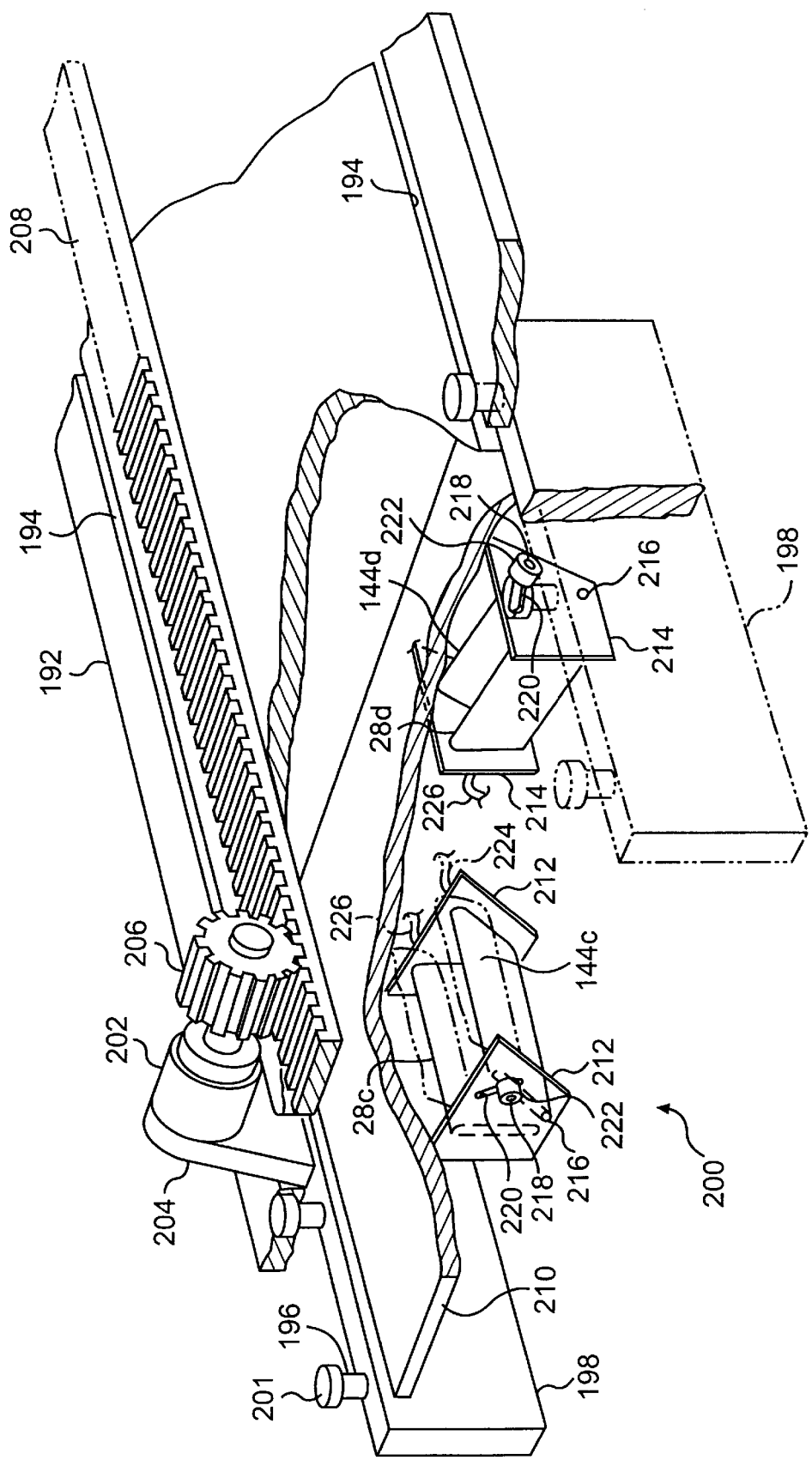
FIG. 19A is a partial perspective view of the optical web defect detection system as in FIG. 18.
Figure 19B:
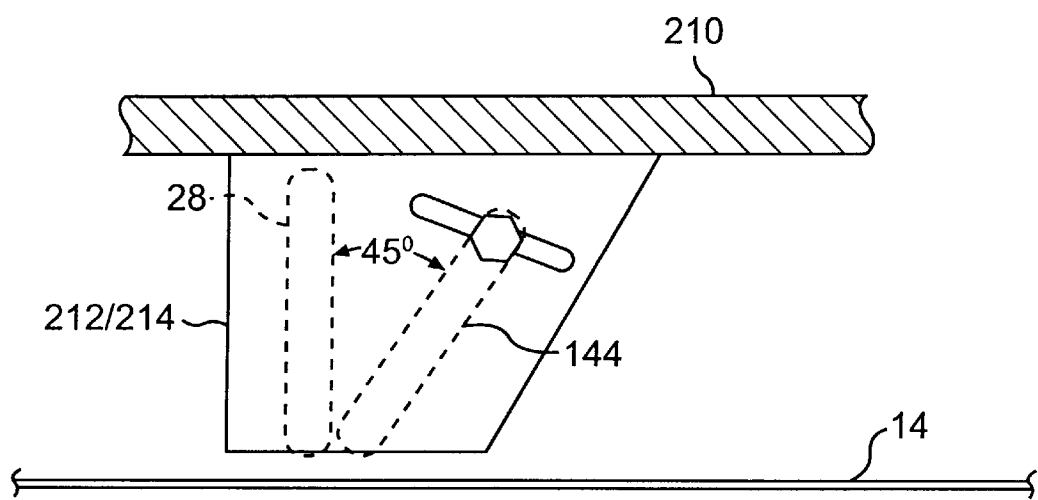
FIG. 19B is a partial side view of the optical web defect detection system as in FIG. 19A.

In a further embodiment shown in FIGS. 18, 19A and 19B, a shift mechanism includes a frame 192 extending across web 14 and including parallel slots 194. Pins 196 extend upward through slots 194 from side members 198 of a carriage 200 so that top flanges 201 vertically secure the carriage on frame 192 while allowing the carriage to slide from one end of the frame to the other.

A motor 202 attached to carriage 200 by a bracket 204 rotationally drives a toothed wheel 206. The teeth of wheel 206 interengage with teeth of a belt 208 attached to frame 192 across the width of web 14. Thus, rotation of wheel 206 by motor 202 moves carriage 200 in a linear path back and forth across the web. In a preferred embodiment, the carriage moves at approximately 1 meter per second.

A top plate 210 extends between side members 198. A first pair of brackets 212 and a second pair of brackets 214 are attached to and extend downward from plate 210. As seen in FIG. 18, brackets 212 are disposed on carriage 200 so that they are aligned with the moving direction 216 of web 14, and brackets 214 are aligned perpendicularly to the moving direction. Respective sensors 28c and 28d and light emitters 144c and 144d extend between brackets 212 and brackets 214. The emitters and sensors are aligned perpendicularly to their brackets. Thus, sensor 28c and light emitter 144c are aligned transversely to the moving direction 216, while sensor 28d and emitter 144d are aligned with the moving direction.

The detection areas of sensors 28c and 28d face directly down toward web 14. That is, considering that the sensors are relatively planar, the planes defined by the sensors are perpendicular to the plane defined by the web. The orientation of the light emitters, however, may vary. Each emitter is pivotally attached at its lower end by pins 216 extending through the respective brackets 212 and 214. They are attached at their upper ends by a pin 218 extending through an arcuate slot 220. Pins 218 and slots 220 may be provided on one or both sides of the light emitter. A cap 222 is threaded onto pin 218 and against the bracket to hold the light emitter into position. Cap 222 may be loosened to pivotally adjust the emitter.

In this embodiment, the light emitters and sensors are the same as those discussed above with respect to FIGS. 12 and 13. Respective fiber optic cables 224 direct light from a light source (not shown) to the emitters. Fiber optic cables 226 carry output signals from the sensors to respective control mechanisms as described above with respect to FIG. 10.

In one preferred embodiment, each emitter is disposed at an approximately 45° angle with respect to its sensor and, therefore, with respect to the web. The light-emitting end of each emitter is disposed adjacent to the detecting surface of its sensor so that the sensor detects light from the emitter reflected directly back from the web. Thus, the angle α (see FIGS. 12 and 13) is approximately 45°. In an alternate configuration, the sensor/emitter pairs may be replaced by bifurcated sensors as in FIG. 14. The bifurcated sensors would be disposed in the positions occupied by the emitters in FIG. 19A.

It should be understood, however, that the emitter and sensor may be disposed in any suitable configuration on the carriage, for example separated from each other as shown in FIG. 13. In this case, each emitter and each corresponding sensor may be attached to the carriage by its own set of brackets.

Referring again to FIG. 18, frame 192 is disposed so that the path of each sensor/emitter pair is disposed at an oblique angle δ with respect to a line 228 perpendicular to the moving direction 216 of web 14. In one preferred embodiment, angle δ is approximately 5° (for example, 4.75°), but may be varied as suitable for a given system. As carriage 200 moves back and forth across the web, the system monitors for longitudinally-aligned defects by sensor 28d (FIG. 19A). The offset angle δ, however, also provides reciprocal movement in the longitudinal direction. Thus, if web 14 is relatively slow moving, as on a loom, the longitudinal shift of carriage 200 increases the relative rate of movement between sensor 28c (FIG. 19A) and transverse defects in the web.

While one or more preferred embodiments of the invention have been described above, it should be understood that any and all equivalent realizations of the present invention are included within the scope and spirit thereof. Thus, the embodiments depicted are presented by way of example only and are not intended as limitations upon the present invention, and those of ordinary skill in this art should understand that many modifications may be made. Therefore, it is contemplated that any and all such embodiments are included in the present invention as may fall within the literal or equivalent scope of the appended claims.

What is claimed is:

1. An optical web defect detection system, said system comprising:
    a light source;
    a detector disposed with respect to said light source so that said detector receives light modulated by a moving web proximate said light source, wherein said detector outputs a signal corresponding at least in part to said modulated light;
    a control mechanism in operative communication with said detector, said control mechanism receiving said signal to detect a defect in said web based thereon; and
    a shift mechanism in operative communication with said detector and configured to reciprocally move said detector in a path parallel to a plane defined by said web and disposed at an oblique angle with respect to a line transverse to the moving direction of said web.

2. The system as in claim 1, wherein said detector includes an elongated optical sensor aligned transversely to the moving direction of said web.

3. The system as in claim 1, wherein said detector includes an elongated optical sensor aligned longitudinally to the moving direction of said web.

4. The system as in claim 1, wherein said path is linear.

5. The system as in claim 1, including a frame extending across said web, a carriage movably disposed on said frame and a drive mechanism in communication with said carriage to reciprocally move said carriage across said web, wherein said detector is disposed on said carriage.

6. The system as in claim 5, including a first said detector having an elongated optical sensor aligned transversely to the moving direction of said web and a second said detector having an elongated optical sensor aligned longitudinally to said moving direction.

7. The system as in claim 1, wherein said oblique angle is approximately 5°.

8. An optical web defect detection system, said system comprising:
    a light source;
    a detector disposed with respect to said light source so that said detector receives light modulated by a moving web proximate said light source, wherein said detector outputs a signal corresponding at least in part to said modulated light;
    a control mechanism in operative communication with said detector, said control mechanism receiving said signal to detect a defect in said well based thereon;
    a frame extending across said web;
    a carriage movably disposed on said frame; and
    a motor in communication with said carriage to reciprocally move said carriage in a path across said web, wherein said detector is disposed on said carriage and wherein said path is disposed at an oblique angle with respect to a line transverse to the moving direction of said web.

9. The system as in claim 8, including a first said detector having an elongated optical sensor aligned transversely to the moving direction of said web and a second said detector having an elongated optical sensor aligned longitudinally to said moving direction.

10. The system as in claim 8, wherein said light source is disposed on said carriage.

11. The system as in claim 10, wherein said light source is disposed on said carriage with respect to said web so that said light source directs light to said web at an oblique angle with respect to a plane defined by said web.

12. The system as in claim 8, wherein said motor is attached to said carriage in driving communication with said frame.

13. A system for handling and inspecting a web of indeterminate length, said system comprising:

a first frame securing said web and moving said web along a path of travel;

a light source;

a second frame extending across said path of travel;

a carriage movably disposed on said second frame;

a motor in communication with said carriage to reciprocally move said carriage in a path disposed across said web at an oblique angle with respect to a line transverse to the moving direction of said web;

a detector disposed on said carriage with respect to said light source so that said detector receives light modulated by said web, wherein said detector outputs a signal corresponding at least in part to said modulated light; and a control mechanism in operative communication with said detector, said control mechanism receiving said signal to detect a defect in said web based thereon.

14. The system as in claim 13, including a first said detector having an elongated optical sensor aligned transversely to said moving direction and a second said detector having an elongated optical sensor aligned longitudinally to said moving direction.

* * * * *